US00PP24931P3

(12) United States Plant Patent
Olesen

(10) Patent No.: US PP24,931 P3
(45) Date of Patent: Sep. 30, 2014

(54) MINIATURE ROSE PLANT NAMED 'POULPAR072'

(50) Latin Name: ***Rosa* hybrid**
Varietal Denomination: Poulpar072

(75) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 180 days.

(21) Appl. No.: 13/507,007

(22) Filed: May 31, 2012

(65) Prior Publication Data

US 2013/0326751 P1 Dec. 5, 2013

(51) Int. Cl.
*A01H 5/00* (2006.01)

(52) U.S. Cl.
USPC ..... Plt./122

(58) Field of Classification Search
CPC ..... A01H 5/0222; A01H 5/0831
USPC ..... Plt./122, 129, 150
See application file for complete search history.

*Primary Examiner* — June Hwu

(57) ABSTRACT

A new miniature rose plant that has abundant, red flowers and attractive foliage. The variety successfully propagates from softwood cuttings and is suitable for year-round production in commercial glasshouses. This new and distinct variety has shown to be uniform and stable in the resulting generations from asexual propagation.

1 Drawing Sheet

Botanical designation: *Rosa* hybrid.
Variety denomination: 'Poulpar072'.

SUMMARY OF THE INVENTION

The present invention constitutes a new and distinct variety of miniature rose plant which originated from a controlled crossing between the female seed parent, an unnamed seedling, and the male pollen parent, also an unnamed seedling.

The two parents were crossed during the summer of 2006 and the resulting seeds were planted in a controlled environment in Fredensborg, Denmark. The new variety, named 'Poulpar072', originated as a single seedling from the stated cross.

The new variety may be distinguished from its male pollen parent and female seed parent primarily by flower coloration and growth habit.

The objective of the hybridization of this rose variety for commercial culture was to create a new and distinct variety with unique qualities, such as:

1. Uniform and abundant red flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

This combination of qualities is not present in previously available commercial cultivars of this type, known to the inventor, and distinguish 'Poulpar072' from all other varieties of which we are aware.

As part of the rose development program, Mogens N. Olesen germinated the seeds from the aforementioned hybridization and conducted evaluations on the resulting seedlings in a controlled environment in Fredensborg, Denmark. 'Poulpar072' was selected by the inventor as a single plant from the progeny of the hybridization in 2006.

Asexual reproduction of 'Poulpar072' by cuttings was first done by Mogens N. Olesen in the nursery in Fredensborg, Denmark in 2007. This initial and other subsequent propagations conducted in controlled environments have demonstrated that the characteristics of 'Poulpar072' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulpar072'. Specifically illustrated in the drawing are flowers at various stages of development, flower in parts, leaves, and stems. Plants photographed are 3 months of age.

DETAILED DESCRIPTION OF THE VARIETY

The following is a description of 'Poulpar072', as observed in its growth in glasshouses in Burlington, Canada. Observed plants are 3 months of age and were cultivated in 10.5 cm pots. Color references are made using The Royal Horticultural Society (London, England) Colour Chart, 2001, except where common terms of color are used.

For a comparison, several physical characteristics of the rose variety 'Poulhappy', U.S. Plant Pat. No. 9,483, are compared to 'Poulpar072' in Chart 1.

CHART 1

| | 'Poulpar072' | 'Poulhappy' |
|---|---|---|
| Petalage: | 30 | 25 to 30 |
| Petal upper side coloration. | Red Group 53C | Red Group 46B |
| Bud color when the sepals first divide | Red-Purple Group 60A | Red Group 46B |

FLOWER AND FLOWER BUD

Blooming habit: Continuous.

Flower bud:

*Size*.—Upon opening, 25 mm in length from base of receptacle to end of bud. 13 mm in diameter.

*Bud form*.—Ovate.

*Bud color*.—As sepals unfold, petals are Red-Purple Group 60A.

*Sepals*.—Upper Surface: Color: Yellow-Green Group 147B. Texture: Smooth, weak pubescence. Lower Surface: Color: Yellow Green Group 147A. Texture: Smooth. Shape: Apex: Cirrhose, somewhat acuminate. Base: Flat at union with receptacle. Margins: Margins have strong foliaceous appendages on three of the five sepals. Size: 30 mm long by 8 mm wide.

*Receptacle*.—Surface Texture: Smooth. Shape: Funnel shaped. Size: 8 mm tall and 8 mm wide. Color: Yellow Green Group 144A.

*Pedicel*.—Surface: Smooth. Many fragrant stipitate glands. Length: 20 mm on average. Diameter: Generally 3 mm. Color: Yellow-Green Group 144A. Strength: Strong.

*Borne*.—Singly.

Flower bloom:

*Fragrance*.—Moderate floral scent.

*Duration*.—As a pot plant, flowers last up to 28 days.

*Size*.—Flower diameter is 45 to 55 mm when open. Flower depth is about 23 mm.

*Form*.—General shape is a hybrid tea with a high pointed center.

*Shape of flower, side view*.—Upon opening, the upper portion is flat. The lower portion is a flat.

Petalage: Under normal conditions, flowers have 30 petals total, 5 of which are petaloids.

Color:

*General tonality*.—On open flower Red Group 53B blended with intonations of Red-Purple Group N57B. As the flowers mature, the color Red-Purple Group N57B becomes more dominant.

*Upon opening, petals*.—Outermost and innermost petals are Red Group 53C on the upper surface. Red-Purple Group 58B on the lower surface. At the base of the petal, the upper surface is Yellow Group 1D, and the lower surface is Yellow Group 1D.

*After opening, petals*.—Outermost and innermost petals are Red Group 53C on the upper surface. Red-Purple Group 58B on the lower surface. At the base of the petal, the upper surface is Yellow Group 1D, and the lower surface is Yellow Group 1D.

Petals:

*Petal reflex*.—Moderate.

*Margin*.—Entire, with moderate undulations.

*Shape*.—Generally ovate. Apex shape: Rounded. Base shape: Rounded.

*Size*.—25 mm (l) by 30 mm (w).

*Texture*.—Smooth.

*Thickness*.—Average.

Petaloids:

*Quantity*.—5 on average.

*Shape*.—Irregular and asymmetric. The apex and base are rounded.

*Color*.—Red Group 53C on the upper surface. Red-Purple Group 58B on the lower surface. At the base of the petaloids, the upper surface is Yellow Group 1D, and the lower surface is Yellow Group 1D.

*Size*.—15 mm (l) by 5 mm (w).

Reproductive organs:

*Pollen*.—None Observed.

*Anthers*.—Size: 2 mm long. Color: Yellow Group 12B. Quantity: 35 on average.

*Filaments*.—Color: Yellow Group 4D. Length: About 3 mm.

*Pistils*.—Length: About 3 mm long. Quantity: 25 on average.

*Stigmas*.—Level relative to the length of the filaments and the height of the anthers. Color: Yellow Group 4D.

*Styles*.—Color: Yellow Group 4D.

*Seed formation*.—Not observed.

PLANT

Plant growth: Upright. Plants are 15 to 20 cm in height, and 15 cm wide.

Stems:

*Color*.—Juvenile growth: Yellow-Green Group 144A. Mature growth: Green Group 146B.

*Length*.—Canes are 12 cm from the base of the plant to the flowering portion.

*Diameter*.—About 3 mm.

*Internodes*.—On mature canes, there is an average distance of 25 mm between nodes.

*Surface texture*.—Young and mature wood is smooth.

Prickles:

*Incidence*.—9 per 10 cm of stem.

*Size*.—Average length is 5 mm.

*Color*.—Juvenile prickles are Greyed-Yellow Group 160A. Mature prickles are Greyed-Orange Group 176C.

*Shape*.—Deeply concave.

Plant foliage:

*Compound leaf size*.—70 mm (l) by 50 mm (w).

*Quantity*.—3 leaves per 10 cm of stem.

*Leaf bearing angle to the stem*.—90 degrees.

*Color of juvenile foliage*.—Upper Leaf Surface: Yellow-Green Group 146A. Lower Leaf Surface: Yellow-Green Group 146B. Anthocyanin: Underneath, Greyed-Red Group 181A covering leaflets.

*Color of mature foliage*.—Upper Leaf Surface: Yellow-Green Group 147A. Lower Leaf Surface: Yellow-Green Group 147B.

Plant leaves and leaflets:

*Stipules*.—Size: About 4 mm in length. Shape: Linear, slightly broad based with outward extending apices. Margins: Finely serrated with few stipitate glands. Color: Yellow-Green Group 144A.

*Petiole*.—Length: 13 mm on average. Diameter: About 1.5 mm. Upper surface: Yellow-Green Group 146A, with intonations of Greyed-Purple Group 183A. Lower surface: Yellow-Green Group 144A. Small prickles.

*Rachis*.—Length: 20 mm on average. Diameter: About 2 mm. Upper surface: Yellow-Green Group 146A with intonations of Greyed-Purple Group 183A. Smooth. Lower surface: Yellow-Green Group 144A.

*Leaflet*.—Number of leaflets: 5 on normal leaves in middle of the stem. Size: 40 mm in length by 22 mm wide. Margin: Serrate. General Shape: Elliptical.

Apex Shape: Acute. Base Shape: Round. Texture: Smooth upper and lower surface. Arrangement: Odd pinnate. Venation: Reticulate. Leaf Gloss: None.

Cold hardiness: The variety is tolerant to USDA Cold Hardiness Zone 6.

Heat tolerance: The variety has been found to be suitable for climate conditions found in the American Horticulture Society heat zone 7.

Disease resistance: Above average resistance to powdery mildew *Sphaerotheca pannosa*, downy mildew *Peronospora sparsa*, rust *Phragmidium* spp., black spot *Diplocarpon rosae,* and *Botrytis cinerea* under normal growing conditions.

The invention claimed is:

1. A new and distinct variety of rose plant of the miniature class named 'Poulpar072', substantially as illustrated and described herein, due to its abundant, red flowers, vigorous growth, compact habit, suitability for production from softwood cuttings in pots, and durable flowers and foliage that make the variety suitable for distribution in the floral industry.

* * * * *

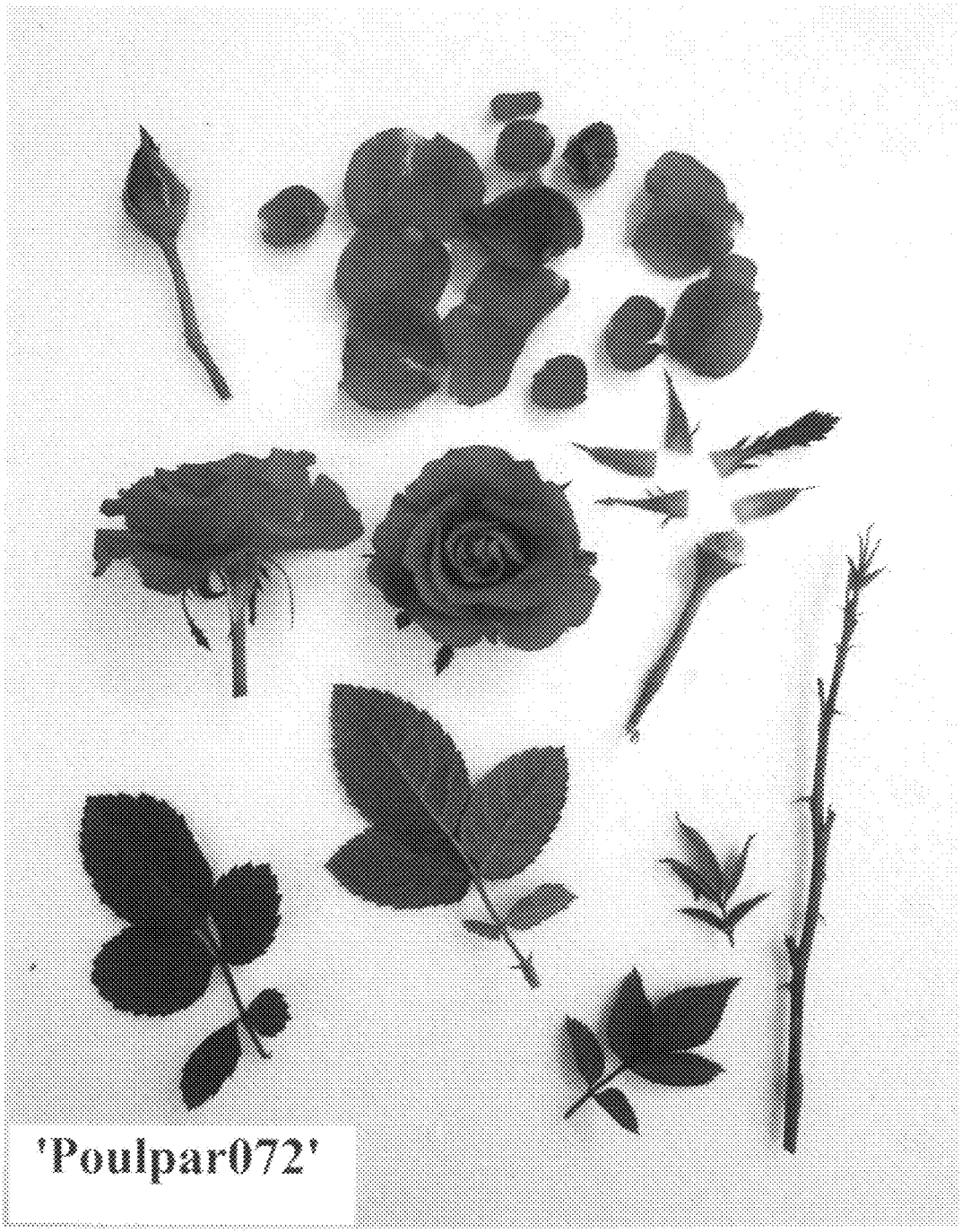
'Poulpar072'